US007917193B2

(12) United States Patent  (10) Patent No.: US 7,917,193 B2
Crane  (45) Date of Patent: Mar. 29, 2011

(54) DETERMINING INSERTED CATHETER END LOCATION AND ORIENTATION

(75) Inventor: Robert L. Crane, Kettering, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 900 days.

(21) Appl. No.: 11/548,318

(22) Filed: Oct. 11, 2006

(65) Prior Publication Data

US 2008/0177174 A1    Jul. 24, 2008

(51) Int. Cl.
*A61B 6/00* (2006.01)
(52) U.S. Cl. .................................. 600/476; 600/473
(58) Field of Classification Search .................. None
See application file for complete search history.

(56) References Cited

U.S. PATENT DOCUMENTS

| 4,567,882 | A | * | 2/1986 | Heller | 600/249 |
| 4,817,622 | A | | 4/1989 | Pennypacker et al. | |
| 5,241,170 | A | | 8/1993 | Field, Jr. et al. | |
| 5,417,688 | A | | 5/1995 | Elstrom et al. | |
| 5,423,321 | A | | 6/1995 | Fontenot | |
| 5,519,208 | A | | 5/1996 | Esparza et al. | |
| 5,718,666 | A | | 2/1998 | Alarcon | |
| 5,907,395 | A | * | 5/1999 | Schulz et al. | 356/139.03 |
| 6,032,070 | A | | 2/2000 | Flock et al. | |
| 6,230,046 | B1 | | 5/2001 | Crane et al. | |
| 6,272,374 | B1 | | 8/2001 | Flock et al. | |
| 6,556,858 | B1 | | 4/2003 | Zeman | |
| 2002/0115922 | A1 | | 8/2002 | Waner et al. | |
| 2003/0187360 | A1 | | 10/2003 | Waner et al. | |
| 2004/0215081 | A1 | | 10/2004 | Crane et al. | |
| 2004/0257007 | A1 | | 12/2004 | Lys et al. | |
| 2005/0070788 | A1 | * | 3/2005 | Wilson et al. | 600/424 |
| 2006/0036164 | A1 | * | 2/2006 | Wilson et al. | 600/424 |
| 2007/0073160 | A1 | * | 3/2007 | Imam | 600/476 |
| 2007/0219451 | A1 | * | 9/2007 | Kula et al. | 600/476 |

* cited by examiner

*Primary Examiner* — Long V Le
*Assistant Examiner* — Angela M Hoffa
(74) *Attorney, Agent, or Firm* — Hasse & Nesbitt LLC; Daniel F. Nesbitt

(57) ABSTRACT

Catheterization device and method of using are provided for uniquely illuminating the distal end of the device in order to visualize the end-point location and orientation and to track the movement of the catheterization device within passageways in the body. Use of the present invention by tracking in real time with an imaging device sensitive to visible to near infrared light. The invention allows the insertion and tracking of substantially any catheterization type device, for substantially any procedure requiring vascular access, such as in the placement of a PICC line, for heart catheterization or angioplasty, or for urinary track catheterization, or other bodily access procedure. The invention permits a technician to determine placement, orientation and movement of the device noninvasive equipment, without subjecting the patient to the hazards associated with ionizing radiation, radio frequency energy or significant thermal energy.

16 Claims, 3 Drawing Sheets

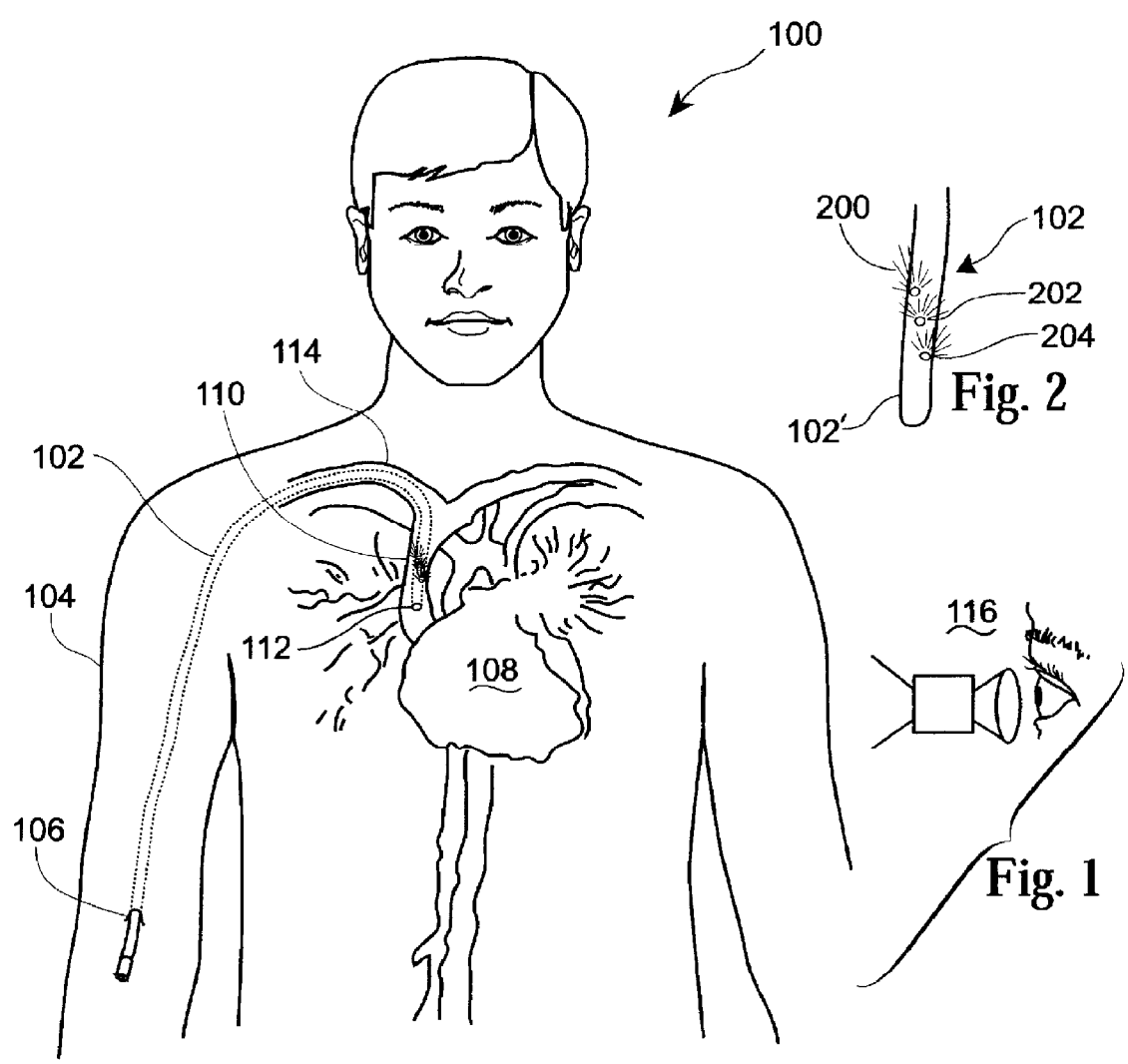

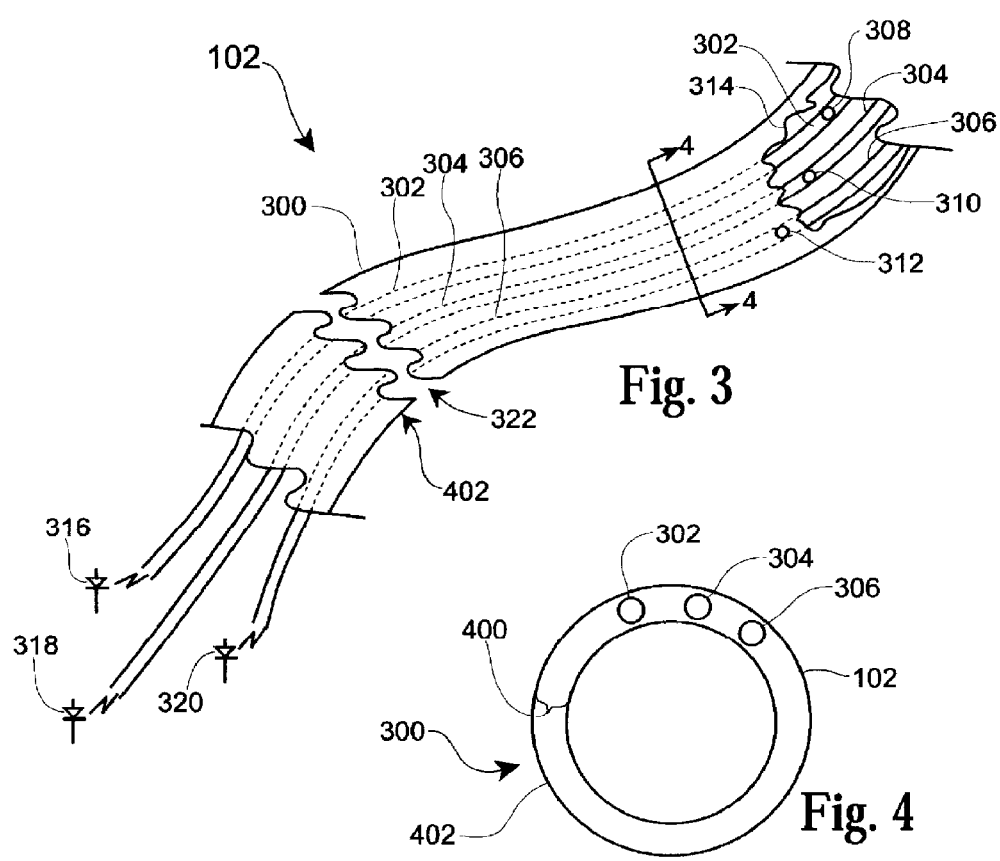
Fig. 3
Fig. 4
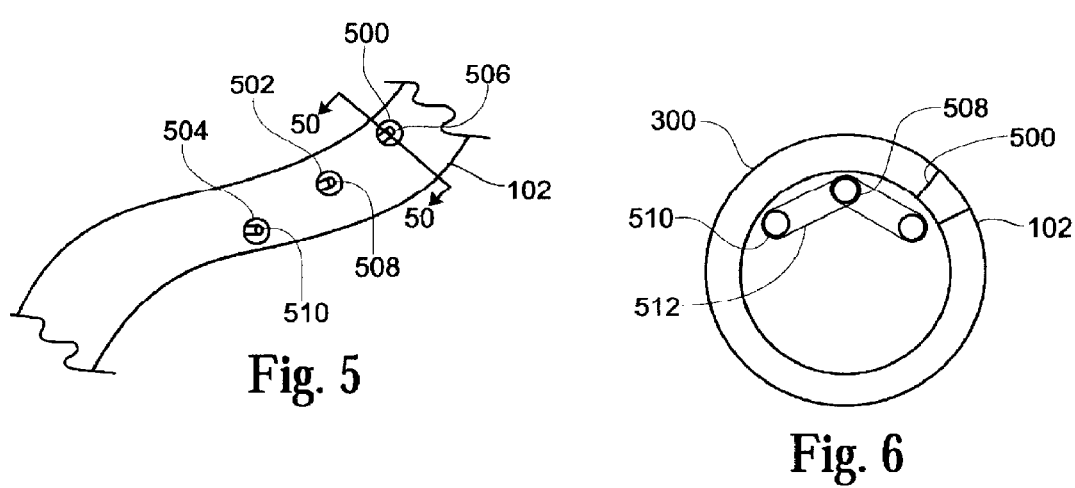
Fig. 5
Fig. 6

DETERMINING INSERTED CATHETER END LOCATION AND ORIENTATION

STATEMENT OF GOVERNMENT INTEREST

The invention described herein was made under a Cooperative Research and Development Agreement number 02-161-ML-01 with the Department of The Air Force. The Government of the United States has certain rights in the invention.

FIELD OF THE INVENTION

The invention described herein relates generally to medical devices and procedures for access to human or animal vasculature, and more particularly to device for vascular access that can be tracked with respect to location and orientation within the vasculature and a procedure for tracking the device.

BACKGROUND OF THE INVENTION

There are frequent medical situations in which it is desirable to insert a device into the vasculature, organ cavity, or other tubular body structure in a human or animal patient for diagnostic or for medical treatment procedures. Example procedures may include the placement of a catheterization or cannulation device into a part of the circulatory system (the vasculature), heart catheterization, urinary track catheterization, angioplasty, among numerous such other medical/diagnostic procedures. Some of these situations involve a short-term placement while others can extend over days or weeks. In the case of a cardiac patient, for example, modern practices often call for the use of a leg inserted arterial catheter and radio opaque dye for early diagnostic purposes or long-term catheter placement for antibiotic medication administration.

One of the difficulties frequently encountered in the placement of such catheters is said to involve the possibility of the catheter not being located in the intended position and in the intended configuration. For example, the moving catheter may follow an intended vein path for a few centimeters and then enter an unintentional branch vein path or double back on itself in a larger vein and thus have a terminal end located in an incorrect position. Because certain drug administration in some situations is location sensitive (because of tissue harm issues) either of these possibilities is undesirable.

In addition to these initial placement issues, the medical community for several reasons favors the placement of peripherally inserted central catheter (PICC) lines within the body as a means of administering treatment as opposed to use of the alternate central venous catheter (CVC) line because of the reduced risk of infection incurred and the fact that the PICC line can be placed by a nursing staff member instead of by a more expensive clinician such as an interventional radiologist. A PICC line can remain in place for many weeks with little concern for systemic infection or other medical complication. PICC treatment is favored because the patient can be placed in the home or low intensity medical facility with this type of line in place.

The PICC line procedure is generally preferred over the CVC procedure for administration of medical treatment. The PICC procedure is not without complication however. The most common difficulty with this procedure is in the uncertainty of the location and the orientation of the PICC line tip. It is not uncommon for a PICC tip to double back on the catheter so that it points in the wrong direction or is pointing into the wrong vein. As a response to this difficulty, a radiologist often confirms the placement of the line after initial insertion using two radiographs. One is take in an antero-posterior orientation and the second in a latero-medial orientation. With these two ninety degree separated views the radiologist can usually discern the location and placement of the distal end of a PICC line.

Unfortunately, however, normal bodily movements can alter the initial orientation and to some extent the placement a thin PICC line. Therefore, it is common for a radiologist to determine the correct placement and orientation of such a line before each treatment or measurement is made. This is time consuming and expensive and carries the added risk to the patient of undesired exposure to ionizing radiation. Therefore, the radiology procedure is often omitted because of reducing patient exposure to x-radiation, limited radiologist time, limited funding, and so-on. A method providing the same information and not requiring radiographic examination is needed.

In addition detection and tracking of catheter or cannulation devices, such as a CVC, in the human body has heretofore been performed by various techniques including the use of x-ray, RF, magnetic resonance, induction and magnetic field, and infrared light. The most common practice is x-ray imaging of a radiopaque cannula that appears in high contrast compared to surrounding structures on a radiographic image. In this procedure the detail and course of the cannula is compared to known structural landmarks of the body, including bone, dense tissue and body margins in order to direct the cannula by x-ray to the intended endpoint. This method can confirm accurate placement of a distal cannula tip terminating in the superior vena cava, but utility of this method is limited if the x-ray exposure time becomes so lengthy as to expose patient and attending practitioner to significant radiation levels.

The distal end of a catheter may also be detected magnetically with a Hall Effect probe or similar magnetic sensor, and may also be detected, though with difficulty, in a space containing air, using ultrasound (U.S. Pat. No. 4,344,436 to Kubota) or radio frequency signals (U.S. Pat. No. 5,377,678 to Dumoulin et al). The general location of the distal end of the catheter can be detected using these methods, but the sensor must be scanned over the patient either during insertion or placement to locate the approximate location of the distal end.

Radio frequency (RF) detection of catheter location, as in U.S. Pat. Nos. 5,377,678 and 5,211,165 to Dumoulin et al, utilizes a transmit coil at the distal end of the catheter, the coil being driven by a low RF energy source that generates an electromagnetic field detectable by either a single or an array of receiver antennae distributed near the body area of interest. A receiver connected to the antennae provides signals that define catheter position and orientation. The positional data are merged with imaging data from radiography to enhance catheter location and orientation in order to minimize overall radiographic exposure. The RF method may, however, result in elevated temperatures in the core of the body during the course of a catheter insertion by way of a diathermy-like process. Utility of the method may be further limited by impedance mismatch between the RF driver and the coil or antenna that limit the strength of signals from the antenna. The procedure also involves both RF and x-ray imaging and thus compounds the instrumentation and operator skills needed to compile location and tracking data and requires x-ray exposure to the patient.

Detection and tracking of catheter location by magnetic resonance (as in U.S. Pat. Nos. 5,307,808 and 5,318,025 to Dumoulin et al, and 5,715,822 to Watkins et al) generally comprises detection of local magnetic resonance response signals via a small RF coil positioned within the body in a larger magnetic resonance field. The patient is subjected to a large-scale magnetic field that induces local responses detected by the small-scale RF coil contained near the catheter distal end. Location is derived from analysis of varying magnetic resonance pulse gradients and requires precision electronics and signal analysis systems, as well as costly computational and imaging tools, including large-scale magnetic resonance imagers with superconducting magnets, and is limited by the short range of the RF coil that allows only limited field-of-view images.

Detection and tracking of a catheter using magnetic coils or objects (as in U.S. Pat. Nos. 4,173,228 to Van Steenwyk et al, 5,125,888 to Howard et al, 5,425,367 to Shapiro et al, 5,645,065 to Shapiro et al, and 6,226,547 to Lockhart et al) generally comprise either measurement of an induced magnetic field in a coil fixed to a catheter within the body or disposed outside the body. At least two interacting component groups are required including at least one energized magnetic output coil and at least one sensor coil to detect the field of the output coils. The output coils may be located near the end of the catheter within the body and the sensor coils near the output components exterior of the body, or the sensors may be affixed to the catheter and the output coils exterior of the body. The exterior sensors must be either scanned over the body or distributed at multiple sites in order to properly measure the strength and orientation of the output signal.

Applying RF energy to coils located within the body potentially exposes the body to large voltages and the associated electric fields that may interfere with body functions or with other monitoring devices. Energizing the sensors outside the body can require a complex arrangement of magnetic transducers that may occupy critical space in the course of medical procedures. In general, such magnetic field detection arrangements rely primarily on proximity between output and sensor components and therefore do not provide complete assessment of the body, but only of portions where exterior components are applied. Furthermore, proximity between components may be difficult to achieve, as a result of physical interference from local or extended medical devices, from materials such as dressings, castings, and electrocardiogram electrodes, from anatomical features such as obesity and dense bone structures and as a result of magnetic fields associated with electrical instrumentation or other or electrical devices.

Detection and tracking of a catheter using near-infrared (NIR) light, is described in U.S. Pat. Nos. 5,517,997 to Fontenot and 6,597,941 to Fontenot et al., and is accomplished using a light guiding catheter inserted into the lumen of, for example, the ureter and involves emitting NIR light from the endpoint of the catheter. Light transilluminating such a ureter is detected by a sensor and highlights the transgressed lumen and surrounding tissue of the body structure. Generally, this method is useful for protection of the transgressed structure or the various body parts lying adjacent to the transgressed regions, and is limited in these particular applications to body intrusive procedures for protection purposes.

SUMMARY OF THE INVENTION

The invention described herein solves or substantially reduces in critical importance several problems associated with prior art catheterization devices by providing a device and a method for uniquely illuminating the catheter distal end in order to visualize the end-point location and orientation and to track the movement of the catheterization device within passageways in the body. Use of the present invention by tracking in real time with an imaging device sensitive to visible to near infrared light, including low level light detectors such as an image intensifier tube, night vision goggle, or charge coupled device (CCD), a metal-on-silicon (MOS) controlled imaging detector, and within certain limits, visible real time imaging with the unaided eye. The invention allows the insertion and tracking of substantially any catheterization type device, for substantially any procedure requiring vascular access, such as in the placement of a PICC line, for heart catheterization or angioplasty, or for urinary track catheterization, or other bodily access procedure. The invention permits a technician to determine placement, orientation and movement of a needle or catheterization or cannulation device with simple, noninvasive equipment, without subjecting the patient to the hazards associated with ionizing radiation, RF energy or significant thermal energy. In addition, the light at the distal end of the device permits visualization of the vasculature passages for branches or other obstructions, such as plaque, and arterial-venous shunts. Helical displacement of the device permits visualization of the vessel around its circumference without having to move or rotate it within the lumen of the vessel.

The invention may be used in medical procedures requiring venal or arterial access for blood sampling or for injection of therapeutic agents or to enable use of PICC lines, catheters or other cannulation type devices instead of the more costly and difficult to administer RF lines. In addition, the invention finds substantial use as an adjunct to aid in the placement of devices during orthoscopic surgical procedures and stints during cardiac catherization, which would result in reduction in x-ray exposure to the patient in comparison to presently used procedures. The invention will permit lesser skilled individuals to perform procedures requiring venal or arterial access, or intubation procedures, in hazardous, dimly lit or primitive situations, such as at an accident site, in an emergency medical vehicle, or on a battlefield.

As used herein, and to permit full appreciation and understanding of the invention and the scope of these teachings and the appended claims, the terms catheter or catheterization device is intended to include any of the medical devices (such as cannulae, catheters, trocars, needles, etc) intended for subcutaneous access to the vasculature (veins, arteries, capillaries, etc) of the body, tubular body structures, organ cavities or intestines, urinary track, or other body passageways, etc, in the practice of medical procedures.

Aspects and advantages of the invention include, but are not necessarily limited to:

an improved mapping arrangement for a body-received catheterization device affording both safety and convenience in its usage;

device and method for accessing veins or arteries for blood sampling or in the administration therapeutic agents;

device and method for venal or arterial access in hazardous, dimly lit or primitive situations;

visualization of location and movement of catheterization devices within the body;

improved accuracy in the insertion and placement of a PICC line;

catheter mapping arrangement free of the difficulties attending previous x-ray, magnetic and RF mapping arrangements;

catheter tracking arrangement indicating both the location and the orientation of a buried distal catheter end node;

catheter tracking arrangement based on the use of innocuous visible spectrum or near visible spectrum radiant energy;

catheter tracking arrangement operable in visible or the near infrared spectral regions;

catheter tracking arrangement usable in a near infrared spectral region of significant transmission window through human tissue; and visualization of the vessel for various pathologic conditions or to determine its structure.

These and other aspects and advantages of the invention are achieved by an improvement in catheterization devices comprising:

a) light conducting means disposed within the catheterization device for transmitting a plurality of light beams along the length of the device from the second end toward the first end, the light conducting means terminating near the first end in a plurality of light emitting locations axially spaced along a terminal segment of the device near the first end;

b) a source of light operatively connected to the second end of the device for transmitting light through the light conducting means toward the light emitting locations; and c) light detection means for detecting light emitted from the plurality of light emitting locations whereby the location of the first end of the device can be determined.

The invention also relates to an improvement in catheterization devices as just described including means for pulsing the source of light whereby the light emitting locations selectively emit light in a predetermined sequence, whereby direction of movement of the device within a passageway of the body can be determined.

The invention further relates to an improvement in catheterization devices wherein the axially spaced light emitting locations are helically disposed around the terminal segment of the device whereby the means for selectively pulsing the source of light determines orientation of the first end of the device within a passageway of the body.

The invention also relates to catheterization device, comprising:

a) an elongated body portion having a first end for insertion into a passageway of the body in the practice of a medical procedure, and a second end;

b) light conducting means disposed within the body portion and along the length thereof for transmitting a plurality of light beams along the body portion from the second end toward the first end, the light conducting means terminating near the first end in a plurality of light emitting locations axially spaced along a terminal segment of the body portion near the first end;

c) a source of light operatively connected to the second end of the body portion for transmitting light along the body portion through the light conducting means toward the light emitting locations;

d) light detection means for detecting light emitted from the light emitting locations whereby the location of the first end of the body portion can be determined; and e) means for pulsing the source of light whereby the light emitting locations selectively emit light in a predetermined sequence, whereby direction of movement of the body portion within a passageway of the body can be determined.

The invention also relates to a catheterization device as just described wherein the axially spaced light emitting locations are helically disposed around the body portion along the terminal segment, whereby the means for selectively pulsing the source of light determines orientation of the first end of the body portion within a passageway of the body.

The invention further relates to a method for determining distal terminal position, direction of movement and orientation of a catheterization device within the body passageways of a patient, comprising the steps of:

a) providing light conducting means within a catheterization device along the length thereof, the light conducting means terminating near a first end of the device in a plurality of light emitting locations axially spaced along a terminal segment of the device;

b) providing a source of light operatively connected to a second end of the device;

c) transmitting light through the light conducting means toward the light emitting locations; and d) detecting light emitted from the light emitting locations whereby the location of the first end of the device can be determined.

The invention further relates to the method just described and further comprising the step of pulsing the source of light whereby the plurality of light emitting locations selectively emit light in a predetermined sequence, whereby direction of movement of the device within a passageway of the body can be determined.

The invention further relates to the method just described wherein the axially spaced light emitting locations are helically disposed around the terminal segment whereby the step of selectively pulsing the source of light determines orientation of the first end within a passageway of the body.

BRIEF DESCRIPTION OF THE DRAWINGS

The invention will be more clearly understood from the following detailed description of representative embodiments thereof read in conjunction with the accompanying drawings.

FIG. 1 illustrates placement and tracking a catheterization or cannulation type device according to the invention.

FIG. 2 shows details of a distal portion of the FIG. 1 device.

FIG. 3 shows additional details of the distal portion of the FIG. 1 device in an enlarged view in partial cutaway.

FIG. 4 shows a view of the FIG. 3 device taken along line 4-4.

FIG. 5 shows a second alternate arrangement of a device as in FIG. 1.

FIG. 6 shows a cross sectional view of the device of FIG. 5.

DETAILED DESCRIPTION OF THE INVENTION

Figure 7:
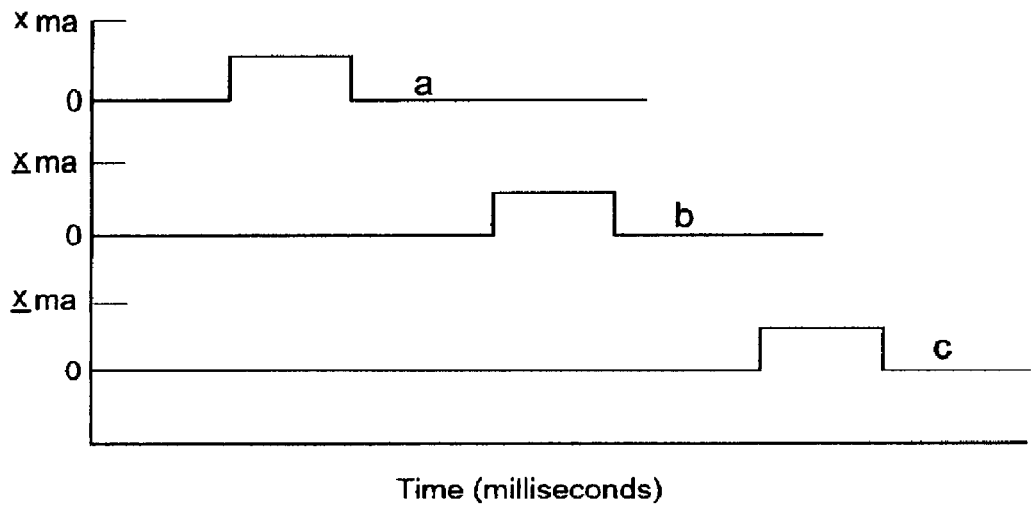
FIG. 7 shows a representative energizing arrangement for light sources usable in the invention exemplified in the figures.

FIG. 1 in the drawings illustrates the placement and tracking within a human patient 100 of a catheterization or cannulation device 102 representative of the present invention. The device 102 is may be configured as substantially any catheterization or cannulation device, or in any other form for substantially any procedure requiring venal or arterial access such as for heart catheterization, angioplasty, or shunt placement or for urinary track catheterization, or other medical procedure requiring access to passageways of the body, such as in vascular, organ or subcutaneous access, the invention is herein described with reference to a representative embodiment of the invention in the form of a peripherally inserted central catheter (PICC) device 102.

In the representative device 102 shown in FIG. 1, and used as a PICC line, the device 102 is usually inserted into one of the large veins in the upper arm 104 near the elbow (e.g., into the basilic vein) by way of a skin opening 106, and is intended to be directed to a target location at the superior vena cava 110 of the heart 108. Such insertion and placement of a PICC line are not, however, trivial procedures, and device 102 can easily end up in unintended locations and configurations proximal to the superior vena cava. For example, device 102 may divert to an unintended vein in the upper arm and proceed back down the arm or may divert into the internal jugular vein. In another embodiment of the invention, the device may take the form of a cardiac catheter for insertion into the femoral artery of the leg in a medical procedure for examining the vasculature to the heart. Other applications or embodiments of the invention within the spirit and scope of these teachings and of the appended claims as applied to various forms of devices for accessing veins and arteries or other body organ ducts as would occur to the skilled artisan practicing the invention will become apparent upon a reading of the description of the invention presented herein.

With reference again to the FIG. 1 representative device, and in accordance with a principal feature of the invention, device 102 will in its structure include two or more light conducting guides for directing light along the length of device 102 from an outside source operatively connected to the proximal end of device 102 toward the distal end 112, the operational details of which are discussed more fully below. Light of substantially any selected wavelength from the visible to the near infrared (NIR) may be used depending on the type of image detector selected for use. Light inserted at the proximal end of device 102 is conducted along the light guides and observed at the distal end 112 as device 102 is urged along vein 114. In the embodiment depicted in FIG. 1 comprising a PICC line, the intended end location for distal end 112 is at superior vena cava 110. Although light of substantially any wavelength could be used, light in the wavelength range of between 650 and 1000 nanometers may be desirable for use with low level light detection means, such as image intensifier tubes, night vision goggles, charge couple devices and the like, in accordance with the teachings of Crane et al (U.S. Pat. No. 6,230,046), incorporated by reference herein. If solid state CCD detectors are used, then a shorter wavelength may be used and optical filtering may be required in order to eliminate extraneous noise from environmental sources such as lighting and broadband optical illuminators. As device 102 is inserted along the intended duct or vasculature, such as vein 102 presented in FIG. 1, the glow at distal end 112 permits assessment of location by way of using conventional anatomical landmarks and intensity of the glow as are observed by, for example, an imaging detector 116. A plurality of optical fibers may be used within the structure of device 102 to conduct light along its length as described more fully below.

A significant aspect of the present invention resides in the usage of multiple light emitters (see FIG. 2 at 200, 202 and 204) at the distal end of device 102, which emitters may be in the form of respective distal ends of the light guides included in the structure of device 102, and, moreover, that these light emitters are operated in a manner allowing external distinction or segregation between the emitters. As may be readily appreciated upon reflection, it is this segregation between the light emitters that allows an outside observer at 116 to comprehend not only the location but also the three-dimensional spatial orientation of the distal end of device 102 even though it is buried in the chest of the patient 100. An easily comprehended and implemented way of providing this distinction or segregation between the emitters at the distal end 112 of device 102 is through use of time segregation of spatially separated light pulses emitted at the distal end 112.

In accordance with this arrangement for identifying three-dimensional spatial location and orientation, FIG. 2 in the drawings shows the distal end portion 112 of device 102 in greater detail. In FIG. 2 it may be observed that device 102 is provided substantially any plurality of light emitters, represented here by the distal ends 200, 202 and 204 of the light guides within device 102 structure, and that are axially spaced and disposed in a substantially helical pattern near the distal end 112 of device 102. With prudent selection of the physical dimensions and the pulsation timing relating to these light emitters, location and orientation of the distal end 112 of device 102 can be ascertained anywhere along the direction of insertion into patient 100.

Referring now to FIG. 3 and FIG. 4, shown therein in an enlarged view are details of a representative structure for the distal portion 112 of the FIG. 1 device 102. The structure of device 102 may include any plurality of light guides represented by the three optical guides (fibers) 302, 304 and 306. The guides may comprise any conventional form as would occur to the skilled artisan practicing the invention, such as, but not limited to, optical fibers of plastic, glass or other optical material know in the optical fiber technology. The optical guides (302, 304, 306) extend from the proximal to distal ends of device 102 with these paths being contained along the wall structure 400 of device 102. The cutaway view at 314 in FIG. 3 shows how the conductors 302, 304 and 306 extend along the full length of device 102, while the break lines at 322 indicate that device 102 may have any reasonable length consistent with the size of patient 100. A plurality of light sources corresponding with the plurality of light guides contained in device 102 provide light of selected wavelength for conducting along the light guides to the distal end 112 of device 102. The three light sources 316, 318 and 320 depicted in FIG. 3 are presented as representative of any plurality of light sources and corresponding light guides that can be included in the structure of the invention, the three sources not considered limiting of the invention or of the appended claims. The light sources may be of substantially any form or construction such as incandescent, photodiode, or other form as would occur to the skilled artisan guided by these teachings, the photodiode being a useful form for inclusion in the invention as providing a range of useful optical wavelengths especially in the near infrared. Device 102 may otherwise be structured conventionally including materials conventionally used for catheterization or cannulation devices in the medical or veterinary arts, such as polymethyl methacrylates, polyesters, various epoxies, glass, plastics, or others, the same not considered limiting of the invention or of the appended claims. As would occur to a skilled artisan practicing the invention, certain of the materials and structural components of the conventional catheterization type device may be used as light conveying elements corresponding to the light guides shown in the figures in an alternative embodiment of the invention.

With reference now specifically to FIG. 3, and in accordance with another aspect of the invention, light conducted along the light guides (such as 302, 304 and 306) may be emitted at locations short of the distal end of device 102. Accordingly, as indicated at 308, 310 and 312, apertures may be axially spaced along the length of the structure of device 102, such as short of the distal 112 of device 102, in order to allow light from the light guides to escape. The apertures may be disposed in a helical configuration as was as axially along the wall 400 of device 102. One manner in which this may be achieved involves interrupting the flow of light along light guides 302, 304 or 306 by way of a minor intrusion such as a mechanical or thermal nicking or cutting of both tubing and conductor so-as to allow the conducted light to escape. The FIGS. 3 and 4 arrangement of device 102 may include light guides built into the wall 400 structure.

FIG. 5 and FIG. 6 show another alternative structural embodiment for the device of the invention wherein the light guides 506, 508 and 510 are disposed within the central bore of the device structure, and the light emitted by these guides is communicated to the outside of the tubing by either transmission through the wall of the tubing or by wall apertures such as are shown at 500, 502 and 504. The aperture 500 also appears in FIG. 6. The light guides 506, 508 and 510 in FIG. 6 may be held in relative position to provide the axial and circumferential (helical) separation between light sources shown in FIG. 1, FIG. 2, FIG. 3 and FIG. 5. This axial and circumferential separation may be provided, for example, by a web 512 of material similar to that of device 102. With suitable materials and procedures, a withdrawal of the light paths 506, 508 and 510 from device 102 after its placement can be accomplished. The FIG. 5 light communicating apertures 500, 502 and 504 may be used to convey light from within device 102 when opaque or light-attenuating materials are used. Apertures 500, 502 and 504 may be positioned in registration with light emitting sources 506, 508 and 510 with, for example, use of illuminated light sources as a positioning guide during forming of the apertures. In FIG. 6 the light source positioning web 512 may be attached temporarily to the wall of tubing 300 by friction/suction or by a thermal connection achieved, for example, during formation of the apertures 500, 502 and 504.

Light scattering by surrounding tissue may require that the exit points for the optical fibers be made to be more widely spaced than if the scattering were not present, and several more than a minimum number of light ports may be provided, since a catheterization line is often trimmed in length because patients are not all of the same physical size. In view of the distal end being the usual location of this trimming or shortening, it is this end that needs extra light ports so that a minimum of three remain when the catheter is shortened.

FIG. 7 shows a series of pulse waveforms indicating the manner in which the three light emitting diodes shown at 316, 318 and 320 in FIG. 3 may be energized in order to produce the sequential pulses of light desired for orientation identification of the distal end 112 of device 102. As indicated by the FIG. 7 waveforms, each of the light emitting diodes 316, 318 and 320 may be operated in its own cycle of energized and non-energized intervals having some selected and optimized (millisecond) duration and some selected magnitude of energized current flow, as are indicated along the horizontal and vertical scales of FIG. 7. Pulse durations measured in milliseconds and current flows measured in milliamperes, as indicated along the horizontal and vertical scale of FIG. 7, are representative of the light source energizing scheme that may be used. Additional details concerning the FIG. 7 waveforms and the timing relationships desired between the FIG. 7 pulses are disclosed in the FIG. 8 drawing and related discussion.

Various details of the FIG. 7 energizing scheme may be altered to suit user needs and preferences and to accommodate the hardware used in energizing the light sources. Such variations include, for example, the overlapping on and off status of individual light sources, the making of one light source brighter or of longer energized time duration than the remaining sources, changes in the number of sources used, as would occur to the skilled artisan practicing the invention.

The letters a, b and c appearing in the FIG. 7 waveforms provide an alternate method of relating the FIG. 7 energizing pulses to light emitting diodes 316, 318 and 320 and light paths 506, 508 and 510. The energizing waveforms shown in FIG. 7 may be accomplished, for example, with use of an electronic counter and decoding circuit arrangement or with use of a series of monostable or one-shot multivibrator electronic circuits each embodied with use of a family of integrated circuits, according to common practice in the electronic circuit art.

The relationship between a series of physically separated blinking lights, the time parameters of the light pulses and the spatial perception conveyed by these lights was investigated in the early 1900's by A. Kort and colleagues in Germany. This investigation led to a concept that is now known as Kort's law, a relationship that may be used in selecting details for the FIG. 7 waveform. Kort's law refers to the physiological relationship between the time interval of several bunking lights and their angular separation and the perception of motion or apparent motion that A Kort outlined in "Kinematoskopische Untersuchungen," (1915). Thus, it may be understood that the timing circuitry that pulses the light sources feeding the optical fibers of the present invention can be adjusted so that Kort's law for apparent motion is maintained and the light pulses seem to point in the direction of distal end 112. While it is not absolutely necessary that this relationship be maintained, it is helpful to do so as an aid to the clinician in mapping the direction of the device's distal end.

Figure 8:
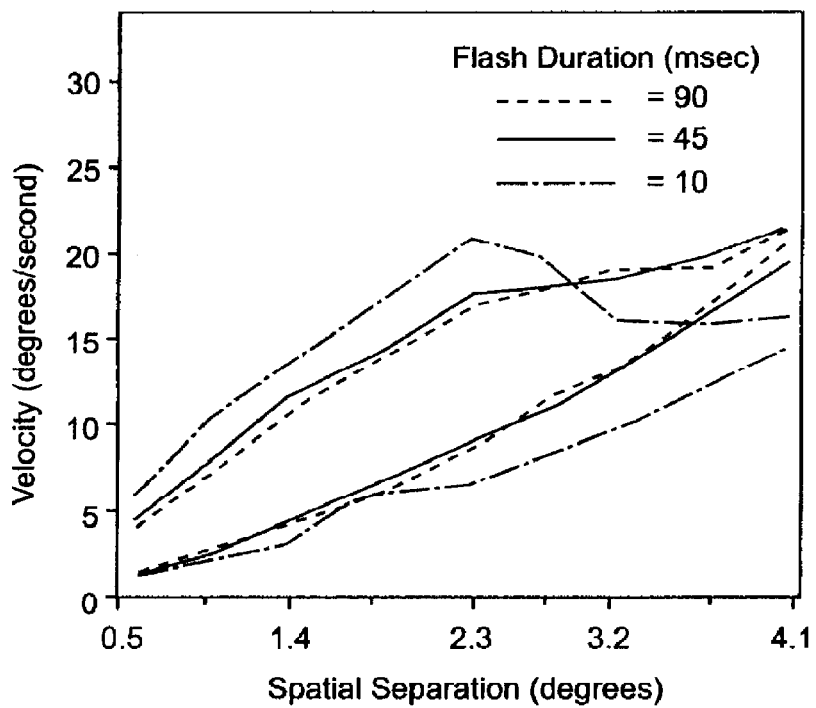
FIG. 8 shows human factors relationships involving blinking of displaced lights considered in selecting parameters suggested in FIG. 7.

The relationship between angular separation and temporal frequency of blinking in these uses and in the present invention is shown in FIG. 8. This drawing is taken from the 1988 report by K. R. Boff & J. E. Lincoln, entitled "Engineering Data Compendium: Human Perception and Performance" published by AAMRL, now the Human Effectiveness Directorate of the Air Force Research Laboratory. FIG. 8 represents a distillation of definitive work in apparent motion. The only modification required in the FIG. 8 data relates to an apparent need for broadening the spatial separation between light sources because the observer is not presented with distinct images of a point source, but instead sees a broad halo caused by the scattering of the overlying tissue between the PICC line and the near infrared detector.

Choosing a specific timing pattern for present invention usage is a matter of user choice. Some practitioners may prefer a slow pointing sequence of blinks, while others may prefer rapid blinking that simulates a smooth transition of light leading or pointing in the direction of the distal end of the device. Additionally, both modes may be implemented at different stages of the insertion process. For example, for the procedure involving the insertion of a PICC line such as depicted in FIG. 1, the slow or sequential blinking mode may be favorable for visualizing the interior of the thoracic cavity and the veins, including any branching in the vascular network. This can be of significant aid in the insertion and guiding of a catheter. During deeper placement when the image is less distinct or even blurred beyond clear recognition, the rapid blinking mode may give the practitioner a better idea of the direction and location of the device's distal end.

The blink rate limits are, of course, bounded by both the static or always-on condition and the condition wherein the blinking appears to be continuous and the practitioner sees only a streak. Relating FIG. 8 to this requires knowledge of the anatomy of the patient, i.e., heavier patients present the practitioner with a more diffuse image earlier in the insertion process and mean that one is high up the ordinate of FIG. 8 because one is farther from the source. In addition, one is farther along the abscissa as the spatial separation in this case is the glow of the NIR light in the patient. The bounds are dictated by the geometry of the observation and scattering properties of the tissue physiology of the patient. The bounds may be ascertained from FIG. 8 wherein the lower set of curves represent optimal motion and the upper set of curves represent the impression of continuous motion for the range of pulse times shown.

The process of the present invention may be performed using a non-imaging apparatus, such as a light sensitive detector at 116 in FIG. 1, to sense infrared light emerging from a patient's torso. In this case, the detector is rastered or scanned in a systematic manner over the body and the location of maximum signal is determined. This is sufficient in many cases for accurate assessment of the location of the distal end of the device. However, a real-time image at 116 can be provided showing the outer surface of the body and the glowing distal end of the catheter. Another tool for making such infrared sourced observations may be found in the viewer disclosed in U.S. Pat. No. 6,230,046 the teachings of which are incorporated by reference herein. Other such tools are found in a set of night vision goggles or other night vision equipment. With sufficiently great levels of illumination in the fiber optic paths of the device, light in the visible part of the spectrum may be used to energize the fiber optic light guides and also sense the emergence of such light in a darkened viewing environment.

The invention therefore provides a novel device and method for particularly illuminating the distal end of a catheter in order to enable location and assessment of progress of insertions and function of various catheterization devices. It is understood that modifications to the invention may be made as might occur to one with skill in the field of the invention within the scope of the appended claims. All embodiments contemplated hereunder that achieve the objects of the invention have therefore not been shown in complete detail. Other embodiments may be developed without departing from the spirit of the invention or from the scope of the appended claims.

What is claimed is:

1. In a catheterization device having a first end for insertion into a passageway of the body in the practice of a medical procedure, and a second end, an improvement comprising:
   (a) light conducting means disposed within said catheterization device for transmitting at least three distinct light beams along the length of said device from said second end toward said first end, said light conducting means terminating near said first end in at least three light emitting locations spaced axially and helically along a terminal segment of said device near said first end;
   (b) a source of at least three lights configured to emit said at least three light beams, each light beam having a wavelength of at least 650 nanometers, wherein said source of at least three lights emit said at least three light beams in distinct cycles of energized and non-energized intervals in accordance with Kort's law for apparent motion, said light source operatively connected to said second end of said device for transmitting said light through said light conducting means toward said light emitting locations; and
   (c) a light detector for detecting light emitted from said at least three light emitting locations and for determining the location of said terminal segment of said device.

2. The improvement of claim 1 further comprising means for pulsing said source of light.

3. The improvement of claim 1 further comprising means for selectively pulsing said source of light.

4. The improvement of claim 1 wherein said light detector is a low level light detector.

5. The improvement of claim 1 wherein said source of light emits light in the wavelength range of from about 650 nanometers to about 1000 nanometers.

6. The improvement of claim 1 wherein said light conducting means comprises optical fibers.

7. A catheterization device, comprising:
   (a) an elongated body portion having a first end for insertion into a passageway of the body in the practice of a medical procedure, and a second end;
   (b) light conducting means disposed within said body portion and along the length thereof for transmitting at least three distinct light beams along said body portion from said second end toward said first end, said light conducting means terminating near said first end in at least three light emitting locations spaced axially and helically along a terminal segment of said body portion near said first end;
   (c) a source of at least three lights configured to emit said at least three light beams, each light beam having a wavelength of at least 650 nanometers, wherein said source of at least three lights emits said at least three light beams in distinct cycles of energized and non-energized intervals in accordance with Kort's law for apparent motion, said light source operatively connected to said second end of said body portion for transmitting said light along said body portion through said light conducting means toward said light emitting locations;
   (d) a light detector for detecting light emitted from said at least three light emitting locations and for determining the location of said terminal segment of said body portion; and
   (e) means for selectively pulsing said source of light.

8. The device of claim 7 wherein said light detector is a low level light detector.

9. The device of claim 7 wherein said source of light emits light in the wavelength range of from about 650 nanometers to about 1000 nanometers.

10. A method for determining distal terminal position, direction of movement and orientation of a catheterization device within the body passageways of a patient, comprising the steps of:
    (a) providing light conducting means within a catheterization device along the length thereof, said light conducting means terminating near a first end of said device in at least three distinct light emitting locations spaced axially and helically along a terminal segment of said device;
    (b) providing a source of at least three lights configured to emit at least three light beams, each light beam having a wavelength of at least 650 nanometers, wherein said source of at least three lights emits said at least three light beams in distinct cycles of energized and non-energized intervals in accordance with Kort's law for apparent motion, said light source operatively connected to a second end of said device;
    (c) transmitting said at least three light beams through said light conducting means toward said at least three light emitting locations; and
    (d) detecting said at least three light beams emitted from said at least three light emitting locations.

11. The method of claim 10 further comprising the step of pulsing said source of light.

12. The method of claim 10 further comprising the step of selectively pulsing said source of light.

13. The method of claim 10 wherein the step of detecting said light emitted from said light emitting locations is performed using a low level light detector.

14. The method of claim 10 wherein said source of light emits light in the wavelength range of from about 650 nanometers to about 1000 nanometers.

15. The method of claim 10 wherein said light conducting means comprises optical fibers.

16. The method of claim 10 wherein said step of detecting said light emitted from said light emitting locations is performed using an infrared sensitive detector.

* * * * *